United States Patent [19]

Watanabe et al.

[11] Patent Number: 5,345,003
[45] Date of Patent: Sep. 6, 1994

[54] METHOD FOR PREPARING 2,3-DICHLORO-1-PROPANOL AND 3-CHLORO-1-PROPANOL

[75] Inventors: Hiroyoshi Watanabe; Fumie Hayakawa, both of Takaishi, Japan

[73] Assignee: Mitsui Toatsu Chemicals, Incorporated, Tokyo, Japan

[21] Appl. No.: 62,755

[22] Filed: May 18, 1993

[30] Foreign Application Priority Data

Jul. 13, 1992 [JP] Japan .................................. 4-184910
Dec. 18, 1992 [JP] Japan .................................. 4-338584

[51] Int. Cl.$^5$ ..................... C07C 29/00; C07C 37/00; C07C 31/34
[52] U.S. Cl. .................. 204/157.9; 568/841
[58] Field of Search .............. 568/841, 844; 204/157.9

[56] References Cited

U.S. PATENT DOCUMENTS 4,788,351 11/1988 Takakuwa et al. .
5,104,504 4/1992 Tanaka et al. .

FOREIGN PATENT DOCUMENTS 2115327 10/1972 Fed. Rep. of Germany .
52-42769 10/1977 Japan .
5-4934 1/1993 Japan .
5-85975 4/1993 Japan .
2129794 5/1984 United Kingdom .

OTHER PUBLICATIONS

J. Chem. Soc. Chem. Commun., 1990, pp. 1334–1335, B. C. Ranu, et al., "Regio–and Stereo–Selective Reductive Cleavage of Epoxides With Zinc Borohydride Supported On Silica Gel".
Patent Abstracts of Japan, vol. 2, No. 67, May 20, 1978, JP-A-53-21111, Feb. 27, 1978.
Patent Abstracts of Japan, vol. 8, No. 251, Nov. 16, 1984, JP-A-59-128341, Jul. 24, 1984.
Patent Abstracts of Japan, vol. 8, No. 251, Nov. 16, 1984, JP-A-59-128340, Jul. 24, 1984.

*Primary Examiner*—Johann Richter
*Assistant Examiner*—Rebecca Cook
*Attorney, Agent, or Firm*—Oblon, Spivak, McClelland, Maier & Neustadt

[57] ABSTRACT

A method for preparing 2,3-dichloro-1-propanol and 3-chloro-1-propanol is here disclosed which comprises the step of reacting 1,2-dichloroethane with methanol by the irradiation of light in the presence of at least one compound selected from the group consisting of europium compounds, samarium compounds and ytterbium compounds, and if necessary, in the additional presence of a zeolite.

11 Claims, No Drawings

METHOD FOR PREPARING 2,3-DICHLORO-1-PROPANOL AND 3-CHLORO-1-PROPANOL

BACKGROUND OF THE INVENTION (i) Field of the Invention

The present invention relates to a method for preparing 2,3-dichloro-1-propanol and 3-chloro-1-propanol.

More specifically, the present invention relates to a method for preparing 2,3-dichloro-1-propanol and 3-chloro-1-propanol by hydroxymethylating 1,2-dichloroethane with methanol. These products are industrially important in themselves or as intermediates of reactions.

(ii) Description of the Prior Art

Since 2,3-dichloro-1-propanol can easily be converted into epichlorohydrin with a caustic alkali or milk of lime, it is useful as a precursor of epichlorohydrin which is a raw material of an epoxy resin and a synthetic rubber. On the other hand, 3-chloro-1-propanol is also a useful substance and industrially important as an intermediate for a reaction.

Nowadays, 2,3-dichloro-1-propanol which is the precursor of epichlorohydrin can be industrially manufactured by a method which comprises chlorinating propylene at a high temperature to form allyl chloride, and then treating allyl chloride with chlorine and water to form a chlorohydrin, or a method which comprises acetoxylating propylene with acetic acid in the presence of a palladium catalyst to form allyl acetate, hydrolyzing allyl acetate to form allyl alcohol, and then chlorinating it. In addition, Japanese Patent Application Laid-open No. 297333/1988 has suggested a method which comprises chlorinating acetone in the presence of an iodine chloride catalyst and a lithium chloride catalyst to form 1,3-dichloroacetone, and then reacting 1,3-dichloroacetone with isopropanol in the presence of an aluminum isopropoxide catalyst.

On the other hand, methods for preparing 3-chloro-1-propanol include a method in which a chloropropanol mixture obtained by treating 1,3-propanediol with hydrogen chloride is subjected to fractional distillation several times [Organic Synthesis Coll. Vol. 1, 533-534 (1964)], a method in which acrolein is reacted with hydrogen chloride in an alcohol to produce an acetal of 3-chloropropionaldehyde, and this acetal is then reduced in the presence of a ruthenium catalyst (Belgian Patent No. 634845), a method in which hydrogen chloride is added to acrolein to form 3-chloropropionaldehyde, and this is then reduced with an alkali metal borate (Japanese Patent Publication No. 42769/1977), and a method in which epichlorohydrin is reduced with zinc borohydride supported on silica gel to obtain a mixture of 3-chloro-1-propanol and propylene chlorohydrin [yield of 3-chloro-1-propanol=60%, J. C. S. Chem. Comm., p. 1334 (1990)].

However, in each of these methods, there are some problems such as the use of the prolonged manufacturing process because of requiring reactions in the several steps, the use of the expensive catalysts and the consumption of a large amount of chlorine for the chlorination of the raw material. Thus, a simple and economical method is desired.

As a method to solve these problems, the present inventors have suggested a method for preparing 2,3-dichloro-1-propanol and 3-chloro-1-propanol by irradiating methanol and 1,2-dichloroethane as starting materials with light in the presence of a peroxide and/or an azo compound (Japanese Patent Application No. 325516/1990), and a method for preparing 2,3-dichloro-1-propanol and 3-chloro-1-propanol by irradiating methanol and 1,2-dichloroethane as starting materials with light in the presence of a carbonyl compound (Japanese Patent Application No. 250700/1991).

These methods in which the reaction is caused to occur by the light irradiation can remarkably simplify the manufacturing process, as compared with a conventional method, but they have the following problems to be solved. That is to say, according to knowledge of the present inventors, in the method in which the light irradiation is done in the presence of the peroxide, the peroxide in an amount equimolar with methanol is required to produce a hydromethyl radical from methanol, and besides danger attends the handling of the peroxide. On the other hand, in the method in which the light irradiation is done in the presence of the azo compound and the method in which the light irradiation is done in the presence of the carbonyl compound, an improvement effect of activation is much lower than in the case of using the peroxide.

SUMMARY OF THE INVENTION

The present inventors have intensively investigated to solve the above-mentioned problems, and as a result, they have found that when 1,2-dichloroethane is reacted with methanol by the irradiation of light in the presence of at least one compound selected from the group consisting of europium compounds, samarium compounds and ytterbium compounds, 1,2-dichloroethane is hydroxymethylated with methanol to form produce 2,3-dichloro-1-propanol and 3-chloro-1-propanol. In consequence, the present invention has now been completed.

In addition, the present inventors have also found that when the above-mentioned reaction is carried out in the presence of a zeolite, a reaction rate and yields of 2,3-dichloro-1-propanol and 3-chloro-1-propanol are remarkably increased.

That is to say, the present invention is directed to a method for preparing 2,3-dichloro-1-propanol and 3-chloro-1-propanol which comprises the step of reacting 1,2-dichloroethane with methanol by the irradiation of light in the presence of at least one compound selected from the group consisting of europium compounds, samarium compounds and ytterbium compounds.

Furthermore, the present invention is also directed to a method for preparing 2,3-dichloro-1-propanol and 3-chloro-1-propanol which comprises the step of reacting 1,2-dichloroethane with methanol by the irradiation of light in the presence of a zeolite and at least one compound selected from the group consisting of europium compounds, samarium compounds and ytterbium compounds.

DETAILED DESCRIPTION OF THE INVENTION

Examples of the europium compounds, samarium compounds and ytterbium compounds which can be used in a method of the present invention include powders of these metals; trivalent oxides, trivalent hydroxides, trivalent fluorides, divalent and trivalent chlorides, trivalent bromides and trivalent iodides of these metals; salts of mineral acids such as trivalent nitrates, trivalent sulfates and trivalent phosphates of these metals; salts of organic acids such as trivalent acetates, trivalent propionates and trivalent oxalates of these metals; alkoxides such as trivalent methoxides, trivalent ethoxides, trivalent isopropoxides and trivalent butoxides of these metals; chelate compounds such as tris(acetylacetonate) salts, tris(heptafluorobutanoylpivaloylmethanate) salts and tris(pivaloyltrifluoroacetonate) salts of these metals; and trivalent carbonates, trivalent perchlorates and trivalent tungstates of these metals.

The europium compounds, samarium compounds and ytterbium compounds may be in the state of anhydrides or hydrates. In particular, the salts of the mineral acids, the salts of the organic acids, the carbonates, the alkoxides and the chelate compounds are preferable.

In the present invention, one compound or plural compounds selected from the group consisting of the europium compounds, samarium compounds and ytterbium compounds can be used.

In the method of the present invention, an amount of the compound selected from the group consisting of the europium compounds, samarium compounds and ytterbium compounds and then used in the reaction is in the range of from 0.01 to 2000 milligram atoms, preferably from 0.1 to 1000 milligram atoms in terms of the total metal atoms based on 1 liter of a liquid phase in the reaction system.

The zeolite which can be used in the method of the present invention is a crystalline aluminosilicate, and examples of the zeolite include shabasite, erionite, offretite, A type zeolite, ferrierite, mordenite, L type zeolite, X type zeolite, Y type zeolite and ZSM-5 type zeolite made by Mobil Co., Ltd. All of $Na^+$ type, $NH_4^+$ type and $H^+$ type of these zeolites are also usable. Particularly, preferable is the zeolite in which $Na^+$ is substituted with a polyvalent ion such as calcium, manganese or a rare earth element by an ion exchange method.

The zeolite may be placed in a reaction vessel without any pretreatment, and it may also be used in the reaction under the light irradiation together with one or more compounds selected from the group consisting of the europium compounds, samarium compounds and ytterbium compounds. Alternatively, prior to the use in the reaction, $Na^+$ in the zeolite may previously be replaced with europium, samarium or ytterbium by the ion exchange method.

An amount of the zeolite to be used is in the range of from 0.01 to 100 parts by weight, preferably from 0.05 to 50 parts by weight based on 1000 parts by weight of a mixture solution comprising at least one compound selected from the group consisting of europium compounds, samarium compounds and ytterbium compounds, 1,2-dichloroethane and methanol.

As the light for the light irradiation in the present invention, there can be used white light having a wide wavelength range of from ultraviolet light to visible light or monochromatic light, but the preferred light is the light generated from a mercury vapor lamp or a flashlamp, or laser beams. With regard to the manner of the light irradiation, a light source may be disposed outside or inside the reaction vessel, and a more effective manner may be selected.

1,2-dichloroethane which can be used as the starting material in the present invention can be inexpensively manufactured usually as a raw material of vinyl chloride by the heat chlorination of ethylene or the oxychlorination of ethylene. With regard to the purity of 1,2-dichloroethane usable in the present invention, a purity of 1,2-dichloroethane for use in the manufacture of usual vinyl chloride is enough.

The other starting material which can be used in the method of the present invention, i.e., methanol can be inexpensively manufactured from carbon monoxide and hydrogen obtained by modifying a petroleum gas or a natural gas. With regard to the purity of methanol usable in the present invention, a purity of methanol containing about 0.1% by weight or less of water for use in the manufacture of usual formalin is enough.

In the present invention, the molar ratio of 1,2-dichloroethane to methanol is in the range of from 0.001 to 100, preferably from 0.01 to 50. If this molar ratio is less than 0.001 or more than 100, a sufficient reaction rate cannot be obtained.

Furthermore, in the method of the present invention, a production ratio between 2,3-dichloro-1-propanol and 3-chloro-1-propanol which are the products can be controlled by changing the molar ratio of 1,2-dichloroethane to methanol which are the starting materials. The molar ratio between the starting materials which can control the production ratio between the products depends upon reacting conditions such as a kind and an amount of catalyst to be used, an intensity of the light source, a distance between the light source and the reactor, and a material of the reactor used in the case of the external irradiation, but when the molar ratio of 1,2-dichloroethane to methanol is about 2 or less, 3-chloro-1-propanol is the main product, and when it is more than 2, 2,3-dichloro-1-propanol is obtained as the main component.

In the method of the present invention, the reaction can proceed, even if any reaction solvent is not used. However, the reaction can also be achieved in the presence of the solvent. Any solvent can be used, so long as it does not have a bad influence on the reaction.

The reaction temperature is in the range of from $-30°$ to $140°$ C., preferably from $0°$ to $100°$ C. If the reaction temperature is lower than $-30°$ C., the reaction rate is insufficient, and if it is higher than $140°$ C., the production of by-products increases. The reaction pressure may be atmospheric pressure or superatmospheric pressure. The reaction time depends upon the intensity of a light source for the light irradiation, the position where the light source is disposed, an irradiation distance, the amount of the starting materials for use in the reaction, the amount of the europium compound, samarium compound or ytterbium compound, and the like, but it is usually in the range of from 10 minutes to 100 hours. If the reaction time is shorter than 10 minutes, a sufficient production cannot be obtained, and if it is longer than 100 hours, much time is taken for the reaction, which is not economical.

The method of the present invention can be achieved by any of a batch process, a semi-batch process and a continuous process. For example, in the case of the batch process, methanol, 1,2-dichloroethane, at least one compound selected from the group consisting of europium compounds, samarium compounds and ytterbium compounds, and if necessary, a zeolite and a reaction solvent are placed in an internal irradiation type light reaction device, and they are then irradiated with light for a predetermined time, so that the reaction proceeds. In the case of the continuous process, methanol, 1,2-dichloroethane, at least one compound selected from the group consisting of europium compounds, samarium compounds and ytterbium compounds, and if necessary, a zeolite and a reaction solvent are continuously fed to one side of the light reaction device, and a reaction mixture which involves unreacted methanol and 1,2-dichloroethane is continuously drawn from the other side of the device, while the reaction is carried out.

According to the method of the present invention, 2,3-dichloro-1-propanol and 3-chloro-1-propanol can be prepared from 1,2-dichloroethane and methanol in one step, and in particular, when the reaction is carried out in the presence of the zeolite, reaction rate and yield can be remarkably improved. Therefore, it is fair to say that the industrial value of the present invention is extremely great.

Now, the present invention will be described in more detail in reference to examples. However, it is to be noted that the scope of the present invention should not be limited to these examples.

EXAMPLE 1

First, 107.3 g (3.35 mols) of methanol, 331.3 g (3.35 mols) of 1,2-dichloroethane and 0.697 g (1.9 mmol) of europium trichloride hexahydrate were placed in a 400 ml inner source typed quartz reaction vessel which is provided with a nitrogen blowing orifice. In this case, the molar ratio of 1,2-dichloroethane to methanol was 1, and the concentration of europium was 5 milligram atoms/liter of a liquid phase. A nitrogen gas was introduced thereinto through the nitrogen blowing orifice to replace the atmosphere in the system with nitrogen, and afterward the system was irradiated internally with a 300 W high pressure mercury lamp at room temperature for 5 hours with stirring under the nitrogen atmosphere to carry out the reaction.

After completion of the reaction, the reaction solution was quantitatively analyzed by gas chromatography, and as a result, it was apparent that 9.53 mmol of 2,3-dichloro-1-propanol (hereinafter abbreviated to "2,3-DCP"), 6.04 mmol of 3-chloro-1-propanol (hereinafter abbreviated to "3-CP") and 11.32 mmol of ethylene glycol (hereinafter abbreviated to "EG") were produced.

EXAMPLE 2

2.5 g (0,078 mol) of methanol, 1.0 g (0.01 mol) of 1,2-dichloroethane and 0.015 g (0.041 mmol) of europium trichloride hexahydrate were placed in a 10 ml Pyrex glass reaction tube having an internal diameter of 8 mm and a height of 20 cm. In this case, the molar ratio of 1,2-dichloroethane to methanol was 0.128, and the concentration of europium was 10 milligram atoms/liter of a liquid phase. Next, the atmosphere in the reaction tube was replaced with nitrogen, and the reaction tube was then sealed. Afterward, the reaction tube was rotated round a 300 W high-pressure mercury vapor lamp in a thermostat tank at 20° C. to carry out reaction. After completion of the reaction, the reaction solution was quantitatively analyzed by gas chromatography, and as a result, it was apparent that 0.02 mmol of 2,3-DCP, 0.07 mmol of 3-CP and 0.05 mmol of EG were produced.

EXAMPLE 3

Reaction and quantitative analysis were carried out by the same procedure as in Example 2 except that the amount of methanol was 2.8 g (0,087 mol) and that of 1,2-dichloroethane was 0.5 g (0.005 mol). As a result, it was apparent that 0.01 mmol of 2,3-DCP, 0.09 mmol of 3-CP and 0.24 mmol of EG were produced.

EXAMPLE 4

Reaction and quantitative analysis were carried out by the same procedure as in Example 2 except that the amount of methanol was 1.6 g (0.050 mol) and that of 1,2-dichloroethane was 2.5 g (0.025 mol). As a result, it was apparent that 0.05 mmol of 2,3-DCP, 0.08 mmol of 3-CP and 0.02 mmol of EG were produced.

EXAMPLE 5

Reaction and quantitative analysis were carried out by the same procedure as in Example 2 except that the amount of methanol was 1.0 g (0.031 mol) and that of 1,2-dichloroethane was 3.3 g (0.033 mol). As a result, it was apparent that 0.05 mmol of 2,3-DCP, 0.05 mmol of 3-CP and 0.02 mmol of EG were produced.

EXAMPLE 6

Reaction and quantitative analysis were carried out by the same procedure as in Example 2 except that the amount of europium trichloride hexahydrate was 0.075 g (0.20 mmol). As a result, it was apparent that 0.01 mmol of 2,3-DCP, 0.02 mmol of 3-CP and 0.11 mmol of EG were produced.

EXAMPLE 7

Reaction and quantitative analysis were carried out by the same procedure as in Example 2 except that the amount of europium trichloride hexahydrate was changed to 0.004 g (0.011 mmol). As a result, it was apparent that 0.01 mmol of 2,3-DCP, 0.03 mmol of 3-CP and 0.10 mmol of EG were produced.

EXAMPLE 8

Reaction and quantitative analysis were carried out by the same procedure as in Example 2 except that a Pyrex glass reaction tube was replaced with a quartz reaction tube. As a result, it was apparent that 0.10 mmol of 2,3-DCP, 0.65 mmol of 3-CP and 1.96 mmol of EG were produced.

EXAMPLE 9

Reaction and quantitative analysis were carried out by the same procedure as in Example 2 except that europium trichloride hexahydrate was replaced with 0.003 g (0.010 mmol) of europium acetate hydrate. As a result, it was apparent that 0.02 mmol of 2,3-DCP, 0.05 mmol of 3-CP and 0.04 mmol of EG were produced.

EXAMPLE 10

Reaction and quantitative analysis were carried out by the same procedure as in Example 2 except that europium trichloride hexahydrate was replaced with 0.005 g (0.014 mmol) of europium perchlorate hexahydrate. As a result, it was apparent that 0.01 mmol of 2,3-DCP, 0.06 mmol of 3-CP and 0.07 mmol of EG were produced.

EXAMPLE 11

Reaction and quantitative analysis were carried out by the same procedure as in Example 2 except that europium trichloride hexahydrate was replaced with 0.002 g (0.010 mmol) of europium carbonate hydrate. As a result, it was apparent that 0.02 mmol of 2,3-DCP, 0.07 mmol of 3-CP and 0.05 mmol of EG were produced.

COMPARATIVE EXAMPLE 1

Reaction and quantitative analysis were carried out by the same procedure as in Example 2 except that europium trichloride hexahydrate was not used. As a result, any product was not detected.

COMPARATIVE EXAMPLE 2

Reaction and quantitative analysis were carried out by the same procedure as in Example 2 except that light irradiation was not given. As a result, any product was not detected.

COMPARATIVE EXAMPLE 3

Reaction and quantitative analysis were carried out by the same procedure as in Example 2 except that 1,2-dichloroethane was not used. As a result, 0.24 mmol of EG was only produced.

EXAMPLE 12

Reaction was carried out by the same procedure as in Example 1 except that europium trichloride hexahydrate was replaced with 0.693 g (1.9 mmol) of samarium chloride hexahydrate.

After completion of the reaction, the reaction solution was quantitatively analyzed by gas chromatography, and as a result, it was apparent that 9.53 mmol of 2,3-DCP, 11.32 mmol of 3-CP and 6.04 mmol of EG were produced.

EXAMPLE 13

1.6 g (0.050 mol) of methanol, 3.8 g (0.038 mol) of 1,2-dichloroethane and 0,018 g (0.05 mmol) of samarium chloride hexahydrate were placed in a 10 ml quartz reaction tube having an internal diameter of 8 mm and a height of 20 cm. In this case, the molar ratio of 1,2-dichloroethane to methanol was 0.76, and the concentration of samarium was 10 milligram atoms/liter of a liquid phase. Next, the atmosphere in the reaction tube was replaced with nitrogen, and the reaction tube was then sealed. Afterward, the reaction tube was rotated round a 300 W high-pressure mercury vapor lamp in a thermostat tank at 20° C. to carry out reaction for 5 hours.

After completion of the reaction, the reaction solution was quantitatively analyzed by gas chromatography, and as a result, it was apparent that 0.03 mmol of 2,3-DCP, 0.11 mmol of 3-CP and 0.02 mmol of EG were produced.

EXAMPLE 14

Reaction was carried out by the same procedure as in Example 13 except that the amount of methanol was 2.8 g (0.087 mol) and that of 1,2-dichloroethane was 0.5 g (0.005 mol).

After completion of the reaction, the reaction solution was quantitatively analyzed by gas chromatography, and as a result, it was apparent that 0.02 mmol of 2,3-DCP, 0.27 mmol of 3-CP and 0.61 mmol of EG were produced.

EXAMPLE 15

Reaction was carried out by the same procedure as in Example 13 except that the amount of methanol was 1.6 g (0.050 mol) and that of 1,2-dichloroethane was 2.5 g (0.025 mol).

After completion of the reaction, the reaction solution was quantitatively analyzed by gas chromatography, and as a result, it was apparent that 0.03 mmol of 2,3-DCP, 0.21 mmol of 3-CP and 0.25 mmol of EG were produced.

EXAMPLE 16

Reaction was carried out by the same procedure as in Example 13 except that the amount of methanol was 1.0 g (0.031 mol) and that of 1,2-dichloroethane was 3.3 g (0.033 mol).

After completion of the reaction, the reaction solution was quantitatively analyzed by gas chromatography, and as a result, it was apparent that 0.04 mmol of 2,3-DCP, 0.06 mmol of 3-CP and 0.01 mmol of EG were produced.

EXAMPLE 17

Reaction was carried out by the same procedure as in Example 13 except that the amount of samarium chloride hexahydrate was changed to 0.037 g (0.10 mmol).

After completion of the reaction, the reaction solution was quantitatively analyzed by gas chromatography, and as a result, it was apparent that 0.02 mmol of 2,3-DCP, 0.09 mmol of 3-CP and 0.01 mmol of EG were produced.

EXAMPLE 18

Reaction was carried out by the same procedure as in Example 13 except that the amount of samarium chloride hexahydrate was changed to 0.004 g (0.010 mmol).

After completion of the reaction, the reaction solution was quantitatively analyzed by gas chromatography, and as a result, it was apparent that 0.01 mmol of 2,3-DCP, 0.04 mmol of 3-CP and 0.01 mmol of EG were produced.

EXAMPLE 19

Reaction was carried out by the same procedure as in Example 13 except that a quartz reaction tube was replaced with a Pyrex glass reaction tube.

After completion of the reaction, the reaction solution was quantitatively analyzed by gas chromatography, and as a result, it was apparent that 0.02 mmol of 2,3-DCP, 0.06 mmol of 3-CP and 0.01 mmol of EG were produced.

EXAMPLE 20

Reaction was carried out by the same procedure as in Example 13 except that samarium chloride hexahydrate was replaced with 0.003 g (0.010 mmol) of samarium acetate (III) hydrate.

After completion of the reaction, the reaction solution was quantitatively analyzed by gas chromatography, and as a result, it was apparent that 0.02 mmol of 2,3-DCP, 0.05 mmol of 3-CP and 0.04 mmol of EG were produced.

EXAMPLE 21

Reaction was carried out by the same procedure as in Example 13 except that samarium chloride hexahydrate was replaced with 0.004 g (0.010 mmol) of samarium perchlorate (III) hexahydrate.

After completion of the reaction, the reaction solution was quantitatively analyzed by gas chromatography, and as a result, it was apparent that 0.01 mmol of 2,3-DCP, 0.06 mmol of 3-CP and 0.07 mmol of EG were produced.

EXAMPLE 22

Reaction was carried out by the same procedure as in Example 13 except that samarium chloride hexahydrate was replaced with 0.005 g (0.010 mmol) of samarium carbonate (III) hydrate.

After completion of the reaction, the reaction solution was quantitatively analyzed by gas chromatography, and as a result, it was apparent that 0.02 mmol of 2,3-DCP, 0.07 mmol of 3-CP and 0.05 mmol of EG were produced.

COMPARATIVE EXAMPLE 4

Reaction was carried out by the same procedure as in Example 13 except that samarium chloride hexahydrate was not used.

After completion of the reaction, the reaction solution was quantitatively analyzed by gas chromatography, and as a result, it was apparent that any product was not detected.

COMPARATIVE EXAMPLE 5

Reaction was carried out by the same procedure as in Example 13 except that light irradiation was not given.

After completion of the reaction, the reaction solution was quantitatively analyzed by gas chromatography, and as a result, it was apparent that any product was not detected.

COMPARATIVE EXAMPLE 6

Reaction was carried out by the same procedure as in Example 13 except that 1,2-dichloroethane was not used.

After completion of the reaction, the reaction solution was quantitatively analyzed by gas chromatography, and as a result, it was apparent that 0.24 mmol of EG was only produced.

EXAMPLE 23

1.6 g (0.050 mol) of methanol, 3.8 g (0.038 mol) of 1,2-dichloroethane and 0.019 g (0.050 mmol) of ytterbium chloride hexahydrate were placed in a 10 ml quartz reaction tube having an internal diameter of 8 mm and a height of 20 cm. In this case, the molar ratio of 1,2-dichloroethane to methanol was 0.76, and the concentration of ytterbium was 10 milligram atoms/liter of a liquid phase. Next, the atmosphere in the reaction tube was replaced with nitrogen, and the reaction tube was then sealed. Afterward, the reaction tube was rotated round a 300 W high-pressure mercury vapor lamp in a thermostat tank at 20° C. to carry out reaction for 5 hours.

After completion of the reaction, the reaction solution was quantitatively analyzed by gas chromatography, and as a result, it was apparent that 0.04 mmol of 2,3-DCP, 0.13 mmol of 3-CP and 0.02 mmol of EG were produced.

EXAMPLE 24

Reaction was carried out by the same procedure as in Example 23 except that the amount of methanol was 2.8 g (0.087 mol) and that of 1,2-dichloroethane was 0.5 g (0.005 mol).

After completion of the reaction, the reaction solution was quantitatively analyzed by gas chromatography, and as a result, it was apparent that 0.02 mmol of 2,3-DCP, 0.63 mmol of 3-CP and 0.16 mmol of EG were produced.

EXAMPLE 25

Reaction was carried out by the same procedure as in Example 23 except that the amount of methanol was 1.6 g (0.050 mol) and that of 1,2-dichloroethane was 2.5 g (0.025 mol).

After completion of the reaction, the reaction solution was quantitatively analyzed by gas chromatography, and as a result, it was apparent that 0.03 mmol of 2,3-DCP, 0.27 mmol of 3-CP and 0.09 mmol of EG were produced.

EXAMPLE 26

Reaction was carried out by the same procedure as in Example 23 except that the amount of methanol was 1.0 g (0.031 mol) and that of 1,2-dichloroethane was 3.3 g (0.033 mol).

After completion of the reaction, the reaction solution was quantitatively analyzed by gas chromatography, and as a result, it was apparent that 0.06 mmol of 2,3-DCP, 0.07 mmol of 3-CP and 0.01 mmol of EG were produced.

EXAMPLE 27

Reaction was carried out by the same procedure as in Example 23 except that the amount of ytterbium chloride hexahydrate was changed to 0.039 g (0.100 mmol).

After completion of the reaction, the reaction solution was quantitatively analyzed by gas chromatography, and as a result, it was apparent that 0.05 mmol of 2,3-DCP, 0.14 mmol of 3-CP and 0.02 mmol of EG were produced.

EXAMPLE 28

Reaction was carried out by the same procedure as in Example 23 except that the amount of ytterbium chloride hexahydrate was changed to 0.004 g (0.010 mmol).

After completion of the reaction, the reaction solution was quantitatively analyzed by gas chromatography, and as a result, it was apparent that 0.02 mmol of 2,3-DCP, 0.05 mmol of 3-CP and 0.01 mmol of EG were produced.

EXAMPLE 29

Reaction was carried out by the same procedure as in Example 23 except that a quartz reaction tube was replaced with a Pyrex glass reaction tube.

After completion of the reaction, the reaction solution was quantitatively analyzed by gas chromatography, and as a result, it was apparent that 0.03 mmol of 2,3-DCP, 0.06 mmol of 3-CP and 0.01 mmol of EG were produced.

EXAMPLE 30

Reaction was carried out by the same procedure as in Example 23 except that ytterbium chloride hexahydrate was replaced with 0.004 g (0.010mmol) of ytterbium acetate (III) hydrate.

After completion of the reaction, the reaction solution was quantitatively analyzed by gas chromatography, and as a result, it was apparent that 0.02 mmol of 2,3-DCP, 0.05 mmol of 3-CP and 0.02 mmol of EG were produced.

EXAMPLE 31

Reaction was carried out by the same procedure as in Example 23 except that ytterbium chloride hexahydrate was replaced with 0.005 g (0.010 mmol) of ytterbium perchlorate (III) hexahydrate.

After completion of the reaction, the reaction solution was quantitatively analyzed by gas chromatography, and as a result, it was apparent that 0.02 mmol of 2,3-DCP, 0.04 mmol of 3-CP and 0.07 mmol of EG were produced.

EXAMPLE 32

Reaction was carried out by the same procedure as in Example 23 except that ytterbium chloride hexahydrate was replaced with 0.004 g (0.010 mmol) of ytterbium nitrate (III) hydrate.

After completion of the reaction, the reaction solution was quantitatively analyzed by gas chromatography, and as a result, it was apparent that 0.02 mmol of 2,3-DCP, 0.07 mmol of 3-CP and 0.04 mmol of EG were produced.

EXAMPLE 33

0.018 g (0.050 mmol) of europium trichloride hexahydrate were placed in a 10 ml quartz reaction tube having an internal diameter of 8 mm and a height of 20 cm, and then dissolved in 2.0 g (0.062 mol) of methanol. Afterward, 30 mg of a ZSM-5 type zeolite (TSZ-841) powder made by Toso Co., Ltd. which had been dried at 200° C. for 10 hours were added thereto and then sufficiently dispersed therein by ultrasonic wave. Next, 1.0 g (0.010 mol) of 1,2-dichloroethane was added thereto, and the atmosphere in the reaction tube was replaced with nitrogen and the reaction tube was then sealed. Afterward, the reaction tube was rotated round a 300 W high-pressure mercury vapor lamp in a thermostat tank at 20° C. to carry out reaction for 5 hours.

After completion of the reaction, the zeolite powder was removed by filtration, and the reaction solution was quantitatively analyzed by gas chromatography. As a result, it was apparent that 0.07 mmol of 2,3-DCP, 0.06 mmol of 3-CP and 0.01 mmol of EG were produced.

EXAMPLE 34

Reaction was carried out by the same procedure as in Example 33 except that TSZ-841 was replaced with 30 mg of a Y type zeolite.

After completion of the reaction, the zeolite powder was removed by filtration, and the reaction solution was quantitatively analyzed by gas chromatography. As a result, it was apparent that 0.06 mmol of 2,3-DCP, 0.05 mmol of 3-CP and 0.01 mmol of EG were produced.

EXAMPLE 35

Reaction was carried out by the same procedure as in Example 33 except that TSZ-841 was replaced with 30 mg of a mordenite powder.

After completion of the reaction, the zeolite powder was removed by filtration, and the reaction solution was quantitatively analyzed by gas chromatography. As a result, it was apparent that 0.06 mmol of 2,3-DCP, 0.05 mmol of 3-CP and 0.01 mmol of EG were produced.

EXAMPLE 36

Reaction was carried out by the same procedure as in Example 33 except that TSZ-841 was replaced with 30 mg of a molecular sieves 13X powder.

After completion of the reaction, the zeolite powder was removed by filtration, and the reaction solution was quantitatively analyzed by gas chromatography. As a result, it was apparent that 0.04 mmol of 2,3-DCP and 0.04 mmol of 3-CP were produced.

EXAMPLE 37

Reaction was carried out by the same procedure as in Example 33 except that europium trichloride hexahydrate was replaced with 0.015 g (0.041 mmol) of samarium trichloride hexahydrate.

After completion of the reaction, the zeolite powder was removed by filtration, and the reaction solution was quantitatively analyzed by gas chromatography. As a result, it was apparent that 0.07 mmol of 2,3-DCP, 0.12 mmol of 3-CP and 0.01 mmol of EG were produced.

EXAMPLE 38

Reaction was carried out by the same procedure as in Example 34 except that europium trichloride hexahydrate was replaced with 0.015 g (0.041 mmol) of samarium trichloride hexahydrate.

After completion of the reaction, the zeolite powder was removed by filtration, and the reaction solution was quantitatively analyzed by gas chromatography. As a result, it was apparent that 0.06 mmol of 2,3-DCP and 0.10 mmol of 3-CP were produced.

EXAMPLE 39

Reaction was carried out by the same procedure as in Example 35 except that europium trichloride hexahydrate was replaced with 0.016 g (0.041 mmol) of ytterbium trichloride hexahydrate.

After completion of the reaction, the zeolite powder was removed by filtration, and the reaction solution was quantitatively analyzed by gas chromatography. As a result, it was apparent that 0.05 mmol of 2,3-DCP and 0.09 mmol of 3-CP were produced.

COMPARATIVE EXAMPLE 7

Reaction was carried out by the same procedure as in Example 33 except that TSZ-841 was not used.

After completion of the reaction, the reaction solution was quantitatively analyzed by gas chromatography, and as a result, it was apparent that 0.03 mmol of 2,3-DCP, 0.03 mmol of 3-CP and 0.01 mmol of EG were produced.

COMPARATIVE EXAMPLE 8

Reaction was carried out by the same procedure as in Example 37 except that TSZ-841 was not used.

After completion of the reaction, the reaction solution was quantitatively analyzed by gas chromatography, and as a result, it was apparent that 0.03 mmol of 2,3-DCP, 0.06 mmol of 3-CP and 0.02 mmol of EG were produced.

COMPARATIVE EXAMPLE 9

Reaction was carried out by the same procedure as in Example 39 except that any mordenite powder was not used.

After completion of the reaction, the reaction solution was quantitatively analyzed by gas chromatography, and as a result, it was apparent that 0.03 mmol of 2,3-DCP, 0.08 mmol of 3-CP and 0.02 mmol of EG were produced.

EXAMPLE 40

There was prepared a device comprising a 190 ml reaction vessel (A) in which a 300 W high-pressure mercury vapor lamp (having a quartz protective tube)

as a light source was inserted into a glass vessel provided with a solution inlet and a solution outlet, a 150 ml wide mouth bottle (B) equipped with a lid having a solution inlet and a solution outlet, and a pump, the vessel (A), the bottle (B) and the pump being connected to each other by Teflon tubes. The solution outlet of the wide mouth bottle (B) was connected to the solution inlet of the glass reaction vessel (A) via the pump, and the solution outlet of the glass reaction vessel (A) was connected to the solution outlet of the wide mouth bottle (B). After the atmosphere in the system was replaced with a nitrogen gas, a material mixture solution comprising 93.40 g (2.92 mol) of methanol, 239.26 g (2.42 mol) of 1,2-dichloroethane and 1.541 g (4.22 mmol) of europium trichloride hexahydrate was placed in the wide mouth bottle (B). In this case, the molar ratio of 1,2-dichloroethane to methanol was 0.83, and the concentration of europium was 10 milligram atoms/liter of a liquid phase. Next, the material mixture solution was forwarded to the glass reaction vessel (A) by means of the tube pump, and the space between the inside cylinder and the outside cylinder was filled with the material mixture solution. The overflow from the glass reaction vessel (A) was introduced into the wide mouth bottle (B), and the reaction temperature in the glass reaction vessel (A) was maintained at 7° C. in a thermostat tank and the reaction solution was irradiated with light for 3 hours to carry out reaction, while the reaction solution was circulated through the above-mentioned route by means of the pump.

After completion of the reaction, the reaction solution was quantitatively analyzed by gas chromatography, and as a result, it was apparent that 7.62 mmol of 2,3-DCP, 12.82 mmol of 3-CP and 6.48 mmol of EG were produced.

EXAMPLE 41

Reaction was carried out by the same procedure as in Example 40 except that the amount of methanol was 67.98 g (2.12 mol) and that of 1,2-dichloroethane was 430.38 g (4.35 mol). In this case, the molar ratio of 1,2-dichloroethane to methanol was 2.05, and the concentration of europium was 10 milligram atoms/liter of a liquid phase.

After completion of the reaction, the reaction solution was quantitatively analyzed by gas chromatography, and as a result, it was apparent that 7.78 mmol of 2,3-DCP, 8.69 mmol of 3-CP and 10.89 mmol of EG were produced.

EXAMPLE 42

Reaction was carried out by the same procedure as in Example 40 except that the amount of methanol was 30.87 g (0.96 mol) and that of 1,2-dichloroethane was 477.29 g (4.82 mol). In this case, the molar ratio of 1,2-dichloroethane to methanol was 5.02, and the concentration of europium was 10 milligram atoms/liter of a liquid phase.

After completion of the reaction, the reaction solution was quantitatively analyzed by gas chromatography, and as a result, it was apparent that 6.30 mmol of 2,3-DCP, 3.34 mmol of 3-CP and 3.24 mmol of EG were produced.

EXAMPLE 43

Reaction was carried out by the same procedure as in Example 40 except that the amount of methanol was 25.82 g (0.81 mol) and that of 1,2-dichloroethane was 490.39 g (4.96 mol). In this case, the molar ratio of 1,2-dichloroethane to methanol was 6.12, and the concentration of europium was 10 milligram atoms/liter of a liquid phase.

After completion of the reaction, the reaction solution was quantitatively analyzed by gas chromatography, and as a result, it was apparent that 13.29 mmol of 2,3-DCP, 2.31 mmol of 3-CP and 2.64 mmol of EG were produced.

EXAMPLE 44

1.27 g (0.04 mol) of methanol, 3.01 g (0.03 mol) of 1,2-dichloroethane, 0.015 g (0.04 mmol) of europium trichloride hexahydrate and 0.009 g (0.04 mmol) of europium dichloride hydrate as catalysts were placed in a 10 ml quartz reaction tube having an internal diameter of 8 mm and a height of 20 cm. In this case, the molar ratio of 1,2-dichloroethane to methanol was 0.75, and the concentration of europium was 20 milligram atoms/liter of a liquid phase. Next, the atmosphere in the reaction tube was replaced with nitrogen, and the reaction tube was then sealed. Afterward, the reaction tube was rotated round a 300 W high-pressure mercury vapor lamp in a thermostat tank at 20° C. to carry out reaction for 5 hours.

After completion of the reaction, the reaction solution was quantitatively analyzed by gas chromatography, and as a result, it was apparent that 0.23 mmol of 2,3-DCP, 0.58 mmol of 3-CP and 0.23 mmol of EG were produced.

EXAMPLE 45

Reaction was carried out by the same procedure as in Example 44 except that 0.015 g (0.04 mmol) of europium trichloride hexahydrate and 0.015 g (0.04 mmol) of samarium trichloride hexahydrate were used as catalysts.

After completion of the reaction, the reaction solution was quantitatively analyzed by gas chromatography, and as a result, it was apparent that 0.18 mmol of 2,3-DCP, 0.46 mmol of 3-CP and 0.25 mmol of EG were produced.

EXAMPLE 46

Reaction was carried out by the same procedure as in Example 44 except that 0.015 g (0.04 mmol) of europium trichloride hexahydrate and 0.016 g (0.04 mmol) of ytterbium trichloride hexahydrate were used as catalysts.

After completion of the reaction, the reaction solution was quantitatively analyzed by gas chromatography, and as a result, it was apparent that 0.16 mmol of 2,3-DCP, 0.51 mmol of 3-CP and 0.21 mmol of EG were produced.

COMPARATIVE EXAMPLE 10

Reaction was carried out by the same procedure as in Example 40 except that europium trichloride hexahydrate was not used.

After completion of the reaction, the reaction solution was quantitatively analyzed by gas chromatography, and as a result, it was apparent that any product was not detected.

COMPARATIVE EXAMPLE 11

Reaction was carried out by the same procedure as in Example 40 except that light irradiation was not given.

After completion of the reaction, the reaction solution was quantitatively analyzed by gas chromatography, and as a result, it was apparent that any product was not detected.

COMPARATIVE EXAMPLE 12

Reaction was carried out by the same procedure as in Example 40 except that 1,2-dichloroethane was not used.

After completion of the reaction, the reaction solution was quantitatively analyzed by gas chromatography, and as a result, it was apparent that 106.21 mmol of EG was only produced.

What is claimed is:

1. A method for preparing 2,3-dichloro-1-propanol and 3-chloro-1-propanol, which comprises the steps of:
reacting 1,2-dichloroethane with methanol, containing no more than 0.1 percent by weight water, in a molar ratio in the range of 0.001 to 100 by exposure to white light of wavelength ranging from ultraviolet light to visible light or monochromatic light at a temperature ranging from $-30°$ to $140°$ C. in the presence of at lest one metal compound catalyst selected from the group consisting of europium compounds, samarium compounds and ytterbium compounds or powdered Eu, Sm or Yb metal, the amount of compound or metal catalyst ranging from 0.01 to 2000 milligrams in terms of the metal atom content of the catalyst per one liter of the liquid phase of the reaction system.

2. The method of claim 1, wherein the catalyst compound is an oxide, hydroxide, fluoride, chloride, bromide, iodide, mineral acid salt, organic acid salt, alkoxide, chelate, carbonate, perchlorate or tungstate of the trivalent metal or the chloride of the divalent metal.

3. The method of claim 1, wherein the molar ratio of 1,2-dichloroethane to methanol ranges from 0.01 to 50.

4. The method of claim 1, wherein the temperature of the reaction ranges from $0°$ to $100°$ C.

5. The method of claim 1, wherein the amount of compound or metal catalyst ranges from 0.1 to 1000 milligram in terms of the metal atom content of the catalyst per 1 liter of the liquid phase of the reaction system.

6. A method for preparing 2,3-dichloro-1-propanol and 3-chloro-1-propanol, which comprises the steps of:
reacting 1,2-dichloroethane with methanol, containing no more than 0.1 percent by weight water, in a molar ratio in the range of 0.001 to 100 by exposure to white light of wavelength ranging from ultraviolet light to visible light or monochromatic light at a temperature ranging from $-30°$ to $140°$ C. in the presence of a zeolite and at least one metal compound catalyst selected from the group consisting of europium compounds, samarium compounds and ytterbium compounds or powdered Eu, Sm or Yb metal, the amount of compound or metal catalyst ranging from 0.01 to 2000 milligrams in terms of the metal atom content of the catalyst per one liter of the liquid phase of the reaction system and the amount of said zeolite ranging from 0.01 to 100 parts by weight of the reaction solution comprising the compound or metal catalyst, 1,2-dichloroethane and methanol.

7. The method of claim 6, wherein the catalyst compound is an oxide, hydroxide, fluoride, chloride, bromide, iodide, mineral acid salt, organic acid salt, alkoxide, chelate, carbonate, perchlorate or tungstate of the trivalent metal or the chloride of the divalent metal.

8. The method of claim 6, wherein the molar ratio of 1,2-dichloroethane to methanol ranges from 0.01 to 50.

9. The method of claim 6, wherein the temperature of the reaction ranges from $0°$ to $100°$ C.

10. The method of claim 6, wherein the amount of compound or metal catalyst ranges from 0.1 to 1000 milligram in terms of the metal atom content of the catalyst per 1 liter of the liquid phase of the reaction system.

11. The method according to claim 2 or 6, wherein the production ratio of 2,3-dichloro-1-propanol to 3-chloro-1-propanol is controlled by changing the molar ratio of 1,2-dichloroethane to methanol.

* * * * *